Figure 1:
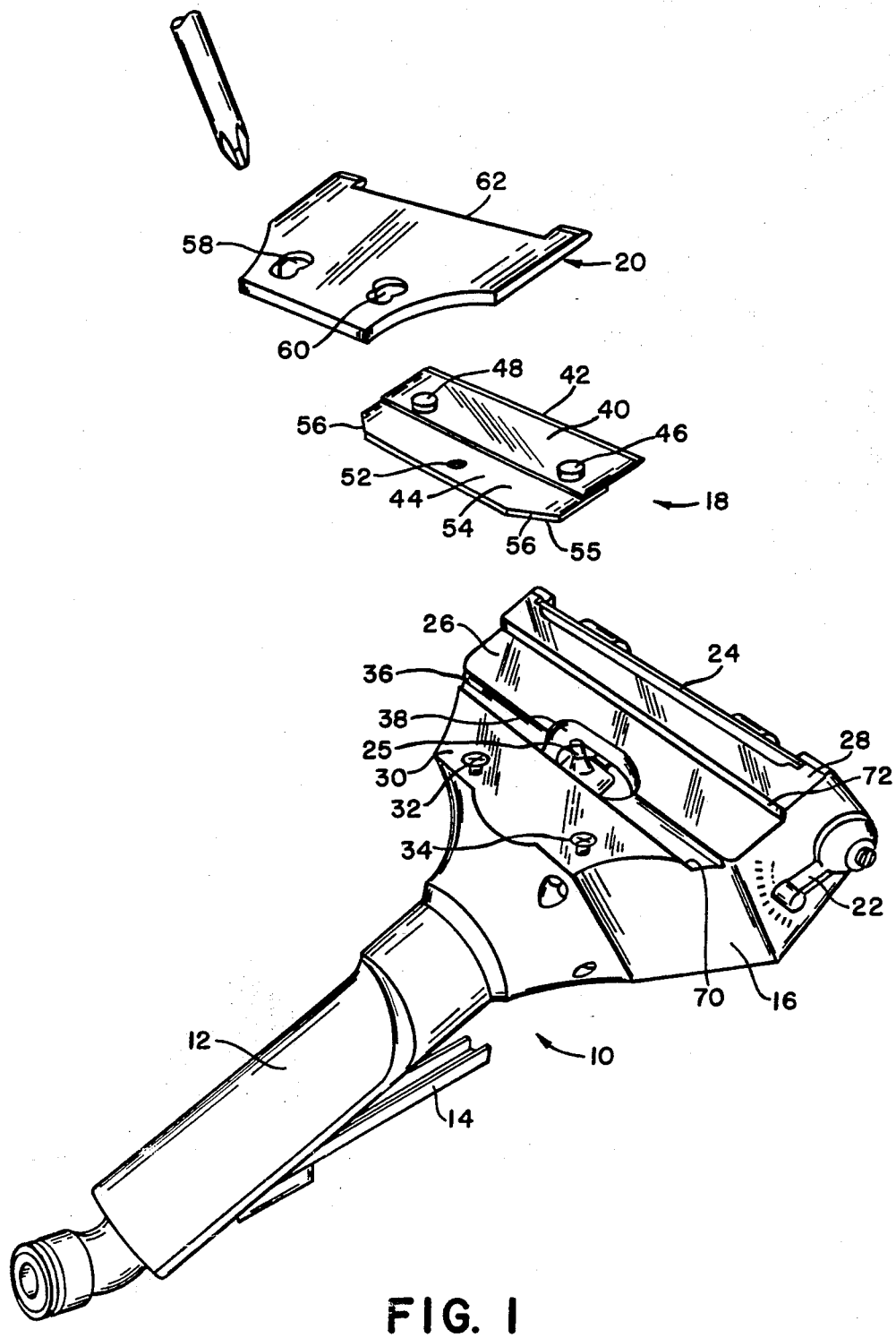

United States Patent [19]

Feltovich et al.

[11] Patent Number: 4,917,086
[45] Date of Patent: Apr. 17, 1990

[54] DERMATOME BLADE ASSEMBLY

[75] Inventors: Susan M. Feltovich; Todd B. Grimm, both of Dover, Ohio

[73] Assignee: Snyder Laboratories, Inc., Dover, Ohio

[21] Appl. No.: 199,226

[22] Filed: May 26, 1988

[51] Int. Cl.$^4$ .......................................... A61B 17/322
[52] U.S. Cl. ..................................... 606/132; 30/223
[58] Field of Search .......... 128/305.5; 30/223, 346.53, 30/346.5, 84, 50

[56] References Cited

U.S. PATENT DOCUMENTS

| | | | |
|---|---|---|---|
| 2,288,709 | 7/1942 | Hood | 128/305 |
| 2,419,114 | 4/1947 | Briegel | 128/305.5 |
| 2,435,278 | 2/1948 | Hood | 128/305.5 |
| 2,457,772 | 12/1948 | Brown et al. | 128/305.5 |
| 2,582,913 | 1/1952 | Pfefferle | 30/346.53 X |
| 2,787,272 | 4/1957 | Groom | 128/305 |
| 3,327,711 | 6/1967 | Vallis | 128/305 |
| 3,412,732 | 11/1968 | Simon | 128/305 |
| 3,428,045 | 2/1969 | Kratzsch | 128/305 |
| 3,488,764 | 1/1970 | Welsh | 30/50 |
| 3,670,734 | 6/1972 | Hardy, Jr. | 128/305 |
| 3,820,543 | 6/1974 | Vanjushim et al. | 128/305 |
| 4,098,278 | 7/1978 | Schwartz | 128/305.5 |
| 4,270,540 | 6/1981 | Schwartz | 128/305.5 |
| 4,628,929 | 12/1986 | Intengan et al. | 128/314 |
| 4,641,429 | 2/1987 | Abatemarco | 30/84 X |
| 4,765,060 | 8/1988 | Veselaski et al. | 30/223 X |

OTHER PUBLICATIONS

"The New and Improved Padgett Dermatome", Padgett Dermatome Ad, 7/1/83.

*Primary Examiner*—Michael H. Thaler
*Attorney, Agent, or Firm*—Paul David Schoenle

[57] ABSTRACT

A dermatome blade assembly includes a first part defining a cutting edge and a second part adapted for reciprocating attachment with a dermatome. The second part is made from a light weight bearing like plastic to minimize vibration and resistance to movement for the blade assembly during operation.

6 Claims, 2 Drawing Sheets

DERMATOME BLADE ASSEMBLY

The present invention relates to a dermatome blade assembly which is used with a dermatone to remove skin from a patient for application elsewhere on the patient to cover a wound or burn. The dermatome is used for cutting a skin graft from a burn patient so that the skin graft can be applied to the burn site to aid in healing.

Several dermatomes are in use today for the purpose of skin grafting. The Padgett Electro Dermatome uses a flat metal blade with a bushing defining an opening to receive a drive member. The flat metal blade defines four sharp corners which may pierce a surgical glove or, even worse, cut the surgeon or nurse while installing or removing the blade from the dermatome. In addition, the flat metal blade is uniformly thin so that it is difficult to grasp when assembled to the dermatome or lying on a flat surface. The Brown Air Dermatome and Brown Electro-Dermatome use a Brown Dermatome TM Blade coupled to a metal blade holder by means of a polymeric adhesive. The polymeric adhesive must be applied across the width of the holder to provide for secure fixation. The Brown metal blade holder provides for easier handling than the Padgett blade; however, the weight of the Brown metal blade and holder is heavy enough that during reciprocating movement of the blade and holder, the Brown Dermatomes may vibrate as skin is being harvested from a patient. This vibration may require a movable counterweight to balance the dermatome such as illustrated in U.S. Pat. No. 3,820,543. The Orthopedic Equipment Company (O.E.C.) blade imitates the metal blade and metal blade holder design of the Brown Dermatome Blade. The two components of the O.E.C. blade are secured together with metal solder. This method introduces lead into the product, poses difficulty in sterilization and increases the probability of the blade breaking off during use. The Hall Air Dermatome uses a blade that is similar to the Padgett flat metal blade but includes a paper tab permitting an operator to grasp the tab without touching the flat metal blade. However, the Hall blade still defines four sharp corners that are capable of piercing gloves.

The present invention teaches a simple light weight dermatome blade assembly which reduces the risk of piercing a glove or cutting an operator's skin as contrasted to the intended cutting and harvesting of skin from a patient. In addition, the dermatome blade assembly forms a bearing surface over the entire width of the assembly to assist with uniform oscillation while skin is being harvested from a patient. The dermatome blade assembly of the present invention includes two parts so that one part can be designed optimally to form a cutting edge while the second part is designed for easy manipulation and attachment of the blade assembly to a dermatome. The second part also provides a bearing surface for smooth reciprocating movement of the blade assembly.

It is an advantage of the present invention that the two-part dermatome blade assembly includes a light weight part to accommodate handling by an operator, attachment to a dermatome, movement during harvesting of skin and connection with a cutting part.

Figure 2:
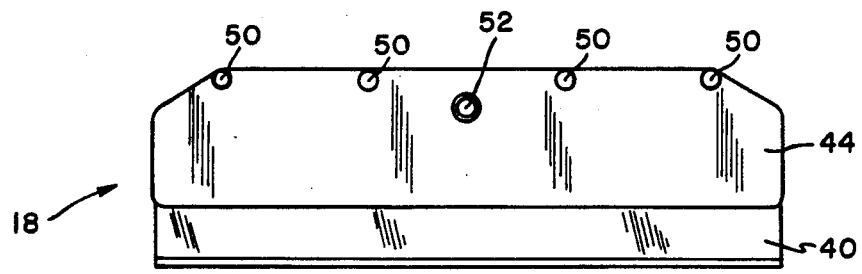
Figure 3:
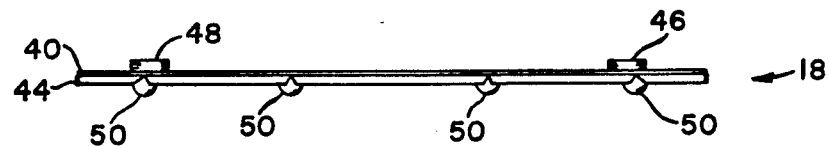

In the drawings FIG. 1 is an exploded view of the dermatome blade assembly in cooperation with a dermatome. FIG. 2 is a bottom view of the dermatome blade assembly. FIG. 3 is a back view of the dermatome blade assembly.

Figure 4:
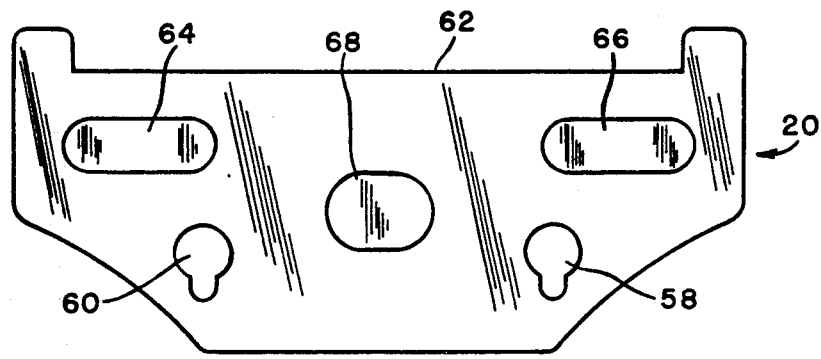
Figure 5:
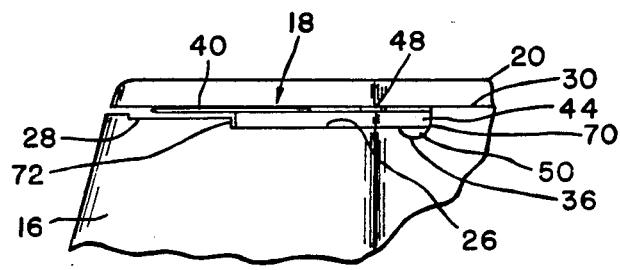

FIG. 4 is a bottom view of the plate which covers the dermatome blade assembly, and FIG. 5 is an enlarged side view of the head of the dermatome with the dermatome blade assembly installed.

When skin is to be harvested from a patient for grafting purposes, the surgeon uses a dermatome 10 to harvest healthy skin. The dermatome 10 includes a handle 12 with a switch 14 for turning the dermatome on and off. A head 16 defines an enlarged transverse width to releasably carry a blade assembly 18 and a plate 20 covering the blade assembly. A lever 22 on the head 16 is coupled to a bar 24 which controls the depth of the skin cut. When the switch is turned on, a drive member 25 reciprocates to impart oscillating movement to the blade assembly 18 so that when the head 16 is scrapped against the healthy skin, the oscillating blade assembly severs the healthy skin from the patient.

The head 16 forms a recess 26 extending across the transverse width to separate a leading face 28 from a trailing face 30. The leading face 28 forms a cut out to receive the bar 24 and the trailing face 30 is provided with threaded bores carrying screws 32 and 34. The recess 26 includes a channel 36 extending across the transverse width and an oblong opening 38 leads to the recess 26 in front of the channel 36 to provide for disposition of the drive member 25 within the recess 26.

The blade assembly 18 comprises a first part 40 defining a cutting edge 42 at one edge of a flat metal plate, and a second part 44 coupled to the first part. The second part is made from a light weight plastic such as white ABS (CYCOLAC T2502) and defines two integral projections which locate and extend through apertures in the first part. The pair of tabs 46 and 48 form enlarged heads which sandwich and securely fasten the first part to the second part at the location of the integral projections. The second part further defines a plurality of posts 50, preferably four, extending in an opposite direction from the tabs 46 and 48, and an opening 52 with a frusto conical wall substantially matching the contour of the drive member 25. The first part 40 is carried on the top surface 54 of the second part 44 with substantially one half or more of the top surface 54 exposed for installation labelling instructions, such as "Insert With This Side Up." Moreover, the exposed portion of the top surface 54 and the bottom surface 55 are easily handled for installation of the blade assembly 18 into the dermatome recess 26. Viewing FIG. 3, the thickness of the second part 44 is about four times thicker than the first part 40. As a result it is easier to pick up and handle the blade assembly by grasping the second part. Although the first part may be touched, the blade assembly is provided with only two corners at the cutting edge which could pierce a glove, and the corners of the second part 44 remote from the cutting edge 42 are chamfered at 56 to match an outer profile for the head 16 and also avoid sharp edges at the point of finger contact.

The plate 20 includes eyelets 58 and 60 cooperating with screws 32 and 34 respectively and a cut out 62 at the leading edge defining the width of cut for the skin to be harvested. Several plates will be used with the blade assembly 18 with each plate including a different width of cut out. The plate 20 includes a pair of depressions 64 and 66 on the side facing the blade assembly 18 so that when the plate is secured via screws 32 and 34 to the trailing face 30, the tabs 46 and 48 will be disposed in the respective depressions for movement therein. A center depression 68 faces the oblong opening 38 so that the drive member 25 remains spaced from the plate 20 even though disposed within the center depression 68.

With the blade assembly 18 disposed within the recess 26, the drive member 25 is fitted within the opening 52 and the four posts 50 are disposed within the channel 36. The blade second part is trapped between recess shoulders 70 and 72 such that the blade assembly 18 can only move in a uniform direction parallel to the shoulders 70 and 72. Moreover, with the second part made of a light weight plastic, the second part acts like a bearing to impart minimum restriction to the reciprocating movement of the blade assembly during operation.

To install the blade assembly 18 to the dermatome 10, a surgeon or surgeon-assistant holds the second part 44 and places the opening 52 over the drive member 25. The second part 44 is snapped onto the drive member to dispose the second part within the recess 26. Next, the plate 20 is placed over the blade assembly with the heads of screws 32 and 34 positioned within the large openings of eyelets 58 and 60. The plate is then moved forwardly toward the bar 24 to align the depressions 64 and 66 with the tabs 46 and 48, respectively and the central depression 68 with that portion of the drive member protruding through the second part opening 52. With the foregoing alignment provided, the plate advances to fully engate the trailing face. The screws 32 and 34 are now disposed within the small openings of eyelets 58 and 60 and the heads of screws 32 and 34 are engageable with the plate to fixedly secure the plate against the trailing face as the screws are tightened. The surgeon sets the lever 22 to the desired depth of cut and the dermatome is turned on to commence harvesting skin from the patient. To remove the blade assembly the above installation steps are reversed.

In view of the foregoing description, the blade assembly 18 is believed to be user friendly with minimal risk of cutting the user or piercing the user's gloves. In addition, the light weight bearing-like plastic second part is ideally suited for uniform reciprocation within the dermatome head.

We claim:

1. A dermatome blade assembly for selective attachment to the dermatome, the blade assembly comprising a two part unit,, a first part of the unit defining a cutting edge adapted for engagement with skin for removal of the latter in response to the reciprocating movement of the first part, the second part being fixedly coupled to the first part at all times and comprising a light weight member adapted for engagement with a reciprocating drive member of the dermatome, the second part further including means cooperating with the dermatome to substantially maintain the reciprocating movement in a parallel direction to the cutting edge and the second part forming a bearing surface movably engaging the dermatome while retaining the first part slightly spaced from the dermatome, the first part forms a first side engageable with the second part and at least one tab extends from the second part through an opening in the first part to form an enlarged head on top of a second side of the first part, and the second part defines at least one post extending in an opposite direction to the one tab and engageable with the dermatome.

2. A dermatome blade assembly comprising a first part forming a cutting edge and a second part secured to the first part to form a unitary assembly for selective attachment to a dermatome, the second part is made from a light weight plastic defining a bearing surface slideably engageable with the dermatome, integral tabs extend outwardly from one surface of the second part to secure the first part to the second part, and at least one post extends outwardly from an opposite surface of the second part to cooperate with the dermatome.

3. A dermatome and blade assembly including at least two parts, a first part of the blade assembly defining a cutting edge adapted for engagement with skin for removal of the latter in response to reciprocating movement of the first part, the second part being coupled to the first part and comprising a light weight member adapted for engagement with a reciprocating drive member of the dermatome, the second part further including means cooperating with the dermatome to substantially maintain the reciprocating movement in a parallel direction to the cutting edge, the second part forming a bearing surface movably engaging the dermatome while retaining the first part slightly spaced from the dermatome, and the dermatome defining a recess to receive the second part to control the direction of movement for the reciprocating two part unit.

4. The dermatome and blade assembly of claim 3 in which a plate is secured to the dermatome to substantially cover the second part and oppose separation of the second part from the drive member.

5. The dermatome and blade assembly of claim 4 in which the plate includes a depression to receive at least one tab extending from the second part through the first part for disposition within the depression.

6. The dermatome and blade assembly of claim 3 in which the dermatome includes a channel opening to the recess and a plurality of posts formed by the second part extend into the channel when the second part is disposed in the recess.

* * * * *
* * * * *